United States Patent [19]

Gustafson et al.

[11] 4,170,646

[45] Oct. 9, 1979

[54] **METHOD FOR THE CONTROL OF *MYCOPLASMA HYOPNEUMONIAE* IN SWINE WITH ALKYLATED BM123γ TYPE ANTIBIOTICS**

[75] Inventors: Richard H. Gustafson, Lawrenceville; Gordon A. Kemp, Princeton, both of N.J.

[73] Assignee: American Cyanamid Company, Stamford, Conn.

[21] Appl. No.: 925,659

[22] Filed: Jul. 17, 1978

[51] Int. Cl.² .................. A61K 31/71; A61K 31/415; A61K 31/35
[52] U.S. Cl. .............................. 424/181; 424/273 R; 424/283; 424/272
[58] Field of Search .......................................... 424/181

[56] References Cited

U.S. PATENT DOCUMENTS

| 4,007,167 | 2/1977 | Martin et al. | 424/181 |
| 4,018,972 | 4/1977 | Hlavka | 424/181 |
| 4,048,431 | 9/1977 | Hlavka et al. | 424/181 |

*Primary Examiner*—Sam Rosen
*Attorney, Agent, or Firm*—H. G. Jackson

[57] ABSTRACT

The invention is a method for the control of *Mycoplasma hyopneumoniae* in swine, comprising administering to the animals parenterally or orally a pharmaceutically effective amount of an alkylated BM123γ type antibiotic or pharmaceutically acceptable salts thereof. The invention further relates to alkylated BM123γ type antibiotics or pharmaceutically acceptable salts thereof, useful for the control of *Mycoplasma hyopneumoniae*.

6 Claims, No Drawings

METHOD FOR THE CONTROL OF *MYCOPLASMA HYOPNEUMONIAE* IN SWINE WITH ALKYLATED BM123γ TYPE ANTIBIOTICS

*Mycoplasma hyopneumoniae* is one of the recognized species of mycoplasmas known to be pathogenic for swine. This disease has also been referred to as virus pneumonia of swine. The only apparent habitat of *M. hyopneumoniae* is the swine lung. It is highly infective and the highest incidence of this disease is to be found usually in finishing house pigs of about 6 months of age and among first litter gilts at about 1 years of age.

*M. hyopneumoniae* is a chronic lung infection with a low rate of mortality. The gross lesions found in the lung of a diseased pig are generally located in the ventral portion of the apical and cardiac lobes, and are characterized by a well demarcated, plum colored area with a "liver-like" consistency. Additionally, there may be enlargement of the mediastinal and other lymph nodes draining the lung.

Obviously, swine affected with the above disease will gain weight much more slowly than healthy pigs, and since the incidence of this disease is usually high in a herd of swine, control of this disease is highly desired.

We now find that by the method of the present invention *Mycoplasma hyopneumoniae* infections in swine can be controlled by administering parenterally or orally to the animals a pharmaceutically effective amount of antibiotic BM123γ represented by formula (I) below:

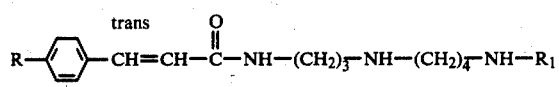

wherein $R_1$ is hydrogen, alkyl $C_1-C_{10}$, alkyl $C_2-C_6$ monosubstituted with halo or hydroxy; and wherein R is a moiety of:

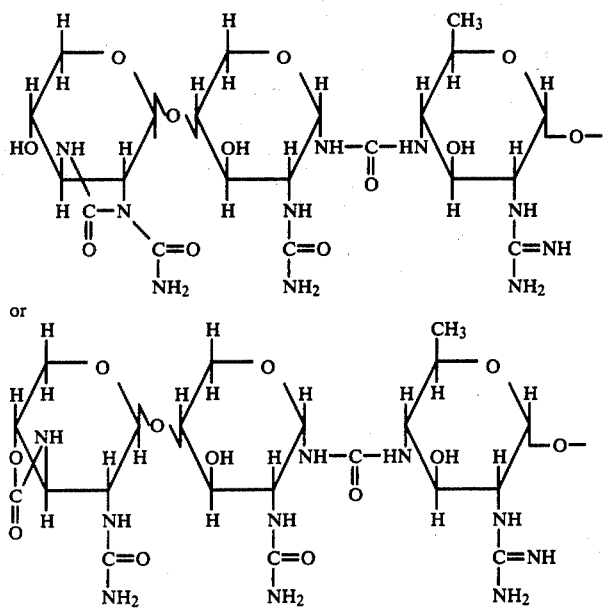

and mixtures thereof; and pharmaceutically acceptable salts thereof.

A preferred group of compounds represented by formula (I) are those, wherein $R_1$ is hydrogen, isopropyl, 1,3-dimethylbutyl, 1,3,3-trimethylbutyl, 1,2-dimethylpentyl, 1-methylnonyl, 1-ethyl-3-chloropropyl or 1-methyl-2-hydroxypropyl.

The most preferred antibiotic of formula (I) is the compound wherein $R_1$ is isopropyl. Hereinafter, this compound is also referred to as isopropyl BM123γ.

Pharmaceutically acceptable acids, which may be used to prepare salts of the above antibiotics, are, among others, hydrochloric acid, sulfuric acid, phosphoric acid, citric acid, tartaric acid, and the like.

The preparation and properties of the above BM123γ antibiotics are set forth in U.S. Pat. No. 4,007,167 (1977), No. 4,018,972 (1977) and No. 4,048,431 (1977).

In accordance with this invention, *Mycoplasma hyopneumoniae* can be effectively controlled by administering a hereinabove identified antibiotic of formula (I), and preferably isopropyl BM123γ to swine in an amount of from about 0.05 mg to 5.0 mg per kg of body weight, and preferably 0.1 mg to 2.0 mg per kg of body weight, in the form of one or more subcutaneous, intramuscular or intravenous injection(s) as required to maintain an effective concentration of the drug in the animals circulatory system until control of *M. hyopneumoniae* is achieved.

In practice, the active material is formulated as injectable(s) using pharmaceutically acceptable solvents, buffers, preservatives and other additives.

Injectables for subcutaneous, intramuscular or intravenous administration may be prepared by dissolving an antibiotic of formula (I), and preferably isopropyl BM123γ, or a pharmaceutically acceptable salt thereof at a concentration of from 1% w/v to 20% w/v, and preferably 1% to 5% w/v in distilled water, wherein the solution may also contain 0.6% to 0.8% w/v of a phosphate or citrate buffer, and the like; 0.4% to 0.6% w/v of sodium chloride, preservatives such as methyl paraben, propyl paraben, and the like, in amounts of from 0.1% to 0.2% w/v, a chelating agent such as disodium edetate, and the like. If desired, some of the water may be replaced in the formulations with water-miscible and pharmaceutically acceptable solvents such as propylene glycol, glycerol, glycerol formal and the like.

Alternatively, a premeasured amount of freeze-dried antibiotic of formula (I) may be prepackaged in multiple unit dosages in sterile vials, and reconstituted with predetermined volumes of sterile water, isotonic saline solution, mixtures of water—propylene glycol, glycerol—glycerol formal, and the like, prior to use.

The following Example is provided to further illustrate the invention.

EXAMPLE 1

In vitro evaluation of the efficacy of BM123γ for the control of *Mycoplasma hyopneumoniae.*

Serial two-fold dilutions of isopropyl BM123γ are made in Friis [N. F. Friis, *Nord. Vet. Med.,* 27:337-39(1975)] broth medium, and 0.05 ml of each is measured into the U shaped wells of micro plates. Next, 0.05 ml of a *Mycoplasma hyopneumoniae* inoculum is added to each of the above dilutions, the micro plates are sealed and carefully agitated to mix the contents of the wells. Samples of inoculated broth, containing no antibiotic are included in the test, as growth controls for each strain tested.

Minimal inhibitory concentrations (MIC) are read as the highest dilution of drug showing no pH change (indicator: phenol red-pH range 6.4-8), i.e. no bacterial growth after 72 hours incubation at 37° C. The results obtained are summarized in Table I below.

TABLE I

| | In vitro efficacy of isopropyl BM123γ for the control of *Mycoplasma hyopneumoniae.* | | |
|---|---|---|---|
| | | MIC (mcg/mil) | |
| Pathogen | No. of Isolates | Range | Median |
| *Mycoplasma hypopneumoniae* | 1 | 0.07 | 0.07 |

We claim:

1. A method for the control of *Mycoplasma hyopneumoniae* in swine, comprising administering parenterally or orally to the animals a pharmaceutically effective amount of antibiotic BM123γ of formula:

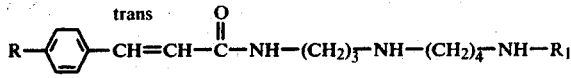

wherein $R_1$ is hydrogen, alkyl $C_1$-$C_{10}$, alkyl $C_2$-$C_6$ monosubstituted with halo or hydroxy; and wherein R is a moiety of:

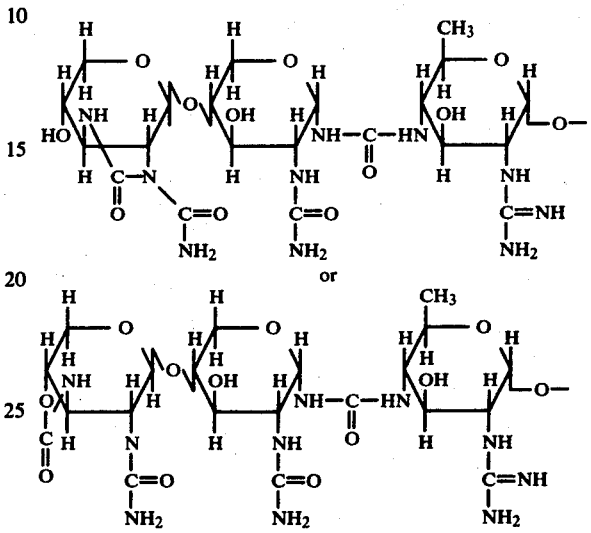

or mixtures thereof; or pharmaceutically acceptable salts thereof.

2. A method according to claim 1 wherein $R_1$ is hydrogen, isopropyl, 1,3-dimethylbutyl, 1,3,3-trimethylbutyl, 1,2-dimethylpentyl, 1-methylnonyl, 1-ethyl-3-chloropropyl or 1-methyl-2-hydroxypropyl.

3. A method according to claim 1, wherein $R_1$ is isopropyl.

4. A method according to claim 1, wherein the salts are hydrochloride, sulfate, phosphate, citrate or tartrate.

5. A method according to claim 1, wherein the compound is administered parenterally in amounts of from 0.05 mg to 5 mg per kg body weight.

6. A method according to claim 1, wherein the compound is isopropyl BM123γ hydrochloride, administered parenterally in amounts of from 0.05 mg to 5 mg per kg body weight.

* * * * *